United States Patent [19]

Hrebeniuk

[11] Patent Number: Plant 6,853

[45] Date of Patent: Jun. 13, 1989

[54] DISTINCT VARIETY OF POINSETTIA NAMED H420C

[76] Inventor: Alexander Hrebeniuk, R.D. #1, Box 118, Sugar Run, Pa. 18846

[21] Appl. No.: 178,335

[22] Filed: Apr. 6, 1988

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Webb, Burden, Ziesenheim & Webb

[57] ABSTRACT

A Poinsettia plant named H420C, particularly characterized by the combined characteristics of bright red and fade resistant bracts, very dark green leaves, triple rows of flat and smooth bracts, medium compact growth habit, and long lasting keeping qualities in the home, and parts therefor.

1 Drawing Sheet

BACKGROUND OF THE NEW PLANT

The present invention comprises a new and distinct cultivar of *Euphorbia pulcherrima* known by the varietal name H420C.

The new cultivar was discovered in November of 1987 as a sport of the cultivar Dynasty (Plant Patent pending). The new cultivar was discovered in Sugar Run, Pa., was first asexually reproduced by cuttings in February of 1988 and has been repeatedly asexually reproduced by cuttings at Sugar Run, Pa. Continued observations of the vegetative cuttings have confirmed that the distinguishing features of this new cultivar come true, remain stable and are retained through successive propagations.

The following traits are determined to be basic characteristics of this new cultivar which, in combination, distinguish this Poinsettia as new and distinct:

1. Nine week response time under black cloth.
2. Four to five breaks after pinch.
3. May be grown single stem or pinch.
4. Top leaves are very dark green.
5. Mature leaves are very dark green.
6. Petioles are very dark red, shiny and waxy.
7. Veins and leaves are light green to red on top and pinkish light green on bottom.
8. Stems on bottom are greenish red, smooth and waxy.
9. Bracts are bright red and very fade resistant in glass greenhouse, plastic house and the home.
10. The centers of the bloom are very tight; cyathia stay up to six (6) weeks.
11. Bloom has three rows of bracts and flat smooth C1 type.
12. Up to eighteen bracts on pinch plant on a single plant and up to 25 bracts on a fully developed bloom.
13. The largest bloom size measured on a single stem plant has been 14 inches in diameter and on a pinch plant 12 inches in diameter.
14. Bracts range in size from 5 cm. to 10 cm. wide and 9 to 15 cm. long on a pinch plant.
15. In normal blooming, the new cultivar shows color by November 15 and the bracts are fully developed by December 10.
16. Responds well to the growth regulator Cycocel.
17. Plants ship well and are long lasting.
18. This cultivar has the ability to grow at temperatures of 65° F. When fully bloomed flower retains its beauty and life at a temperature of 60° F. and has non-drooping foliage.

DESCRIPTION OF THE DRAWINGS

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The plant history was taken on nine week plants. The color readings were determined at 1:30 p.m. on Feb. 3, 1988 under natural daylight at Sugar Run, Pa. Color references are primarily to the R.H.S. Colour Chart of The Royal Horticultural Society of London.

The plant:

*Form.*—Triple.

*Growth habit.*—Medium and compact.

*Rooting.*—Very fast; very uniform.

*Blooming season.*—Nine weeks.

*Blooming habit.*—Large bracts in triple layer.

Foliage:

*Size.*—By pinch plant 7 cm. wide and 12 cm. long.

*Quantity.*—Up to nine leaves per stem depending on culture. Color — New foliage — Upper side, Green Group 139A. Under side, Green Group 139B. Old foliage — Upper side, Green Group 139A. Under side, Green Group 139B. Leaf petiole — Red Group 46A.

*Shape.*—Pinch plant, heart shape to oak shaped.

*Texture.*—The upper side is waxy and smooth; under side is rough because of veins.

*Edge of margin.*—Wavy.

*Aspect.*—Varies from nearly horizontal to upwardly and downwardly inclined.

*Veins.*—Midrib to margin.

*Disease resistance.*—Very resistant to Botrytis.

Flower: Cyathia.

*Borne.*—Single, very compact, inflorescence.

*Quantity.*—No more than 12; each one has a nectary.

*Color.*—Varies widely depending on stage of development; generally light orange to orange-red when mature.

Bracts:

*Size.*—5 cm. wide and 9 cm. long when immature to 10 cm. wide and 15 cm. long when fully grown on pinch plant.

*Veins.*—Midrib to margin.

*Quantity.*—On pinch plant up to 18 bracts on single plant; 25 bracts have been counted on a fully developed bloom.

*Color.*—Top: Red Group 46 C. Bottom: Red Group 46 D.

*Resistance to fade.*—Excellent, long lasting in the home.

Reproductive organs: Typical for Poinsettia cultivars.

I claim:

1. A new and distinct variety of Poinsettia plant as herein shown and described and particularly characterized by its bright red and fade resistant bracts, very dark green leaves, triple rows of flat and smooth bracts, medium compact growth habit, and long lasting keeping qualities in the home, and parts therefor.

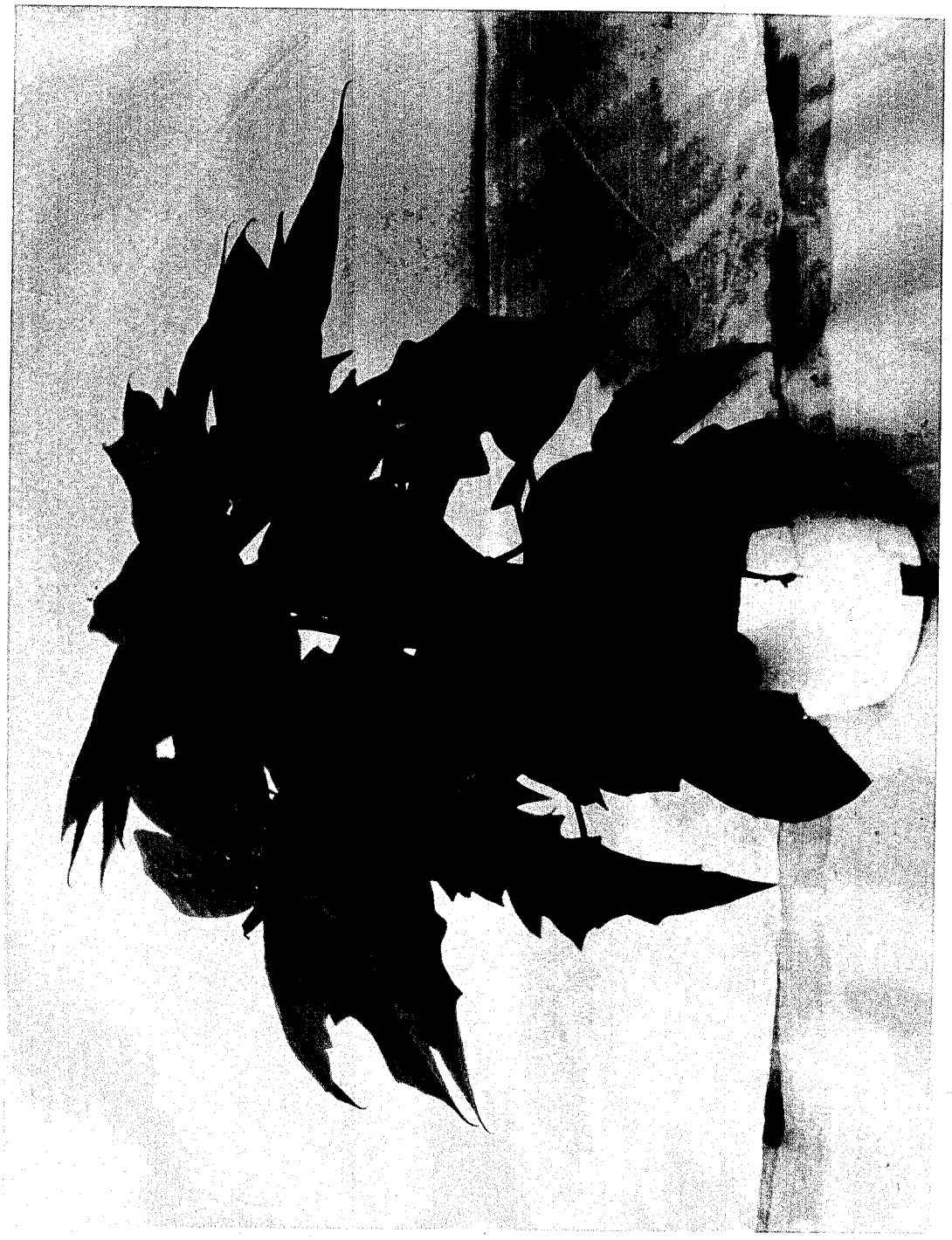

* * * * *